(12) United States Patent
Siess et al.

(10) Patent No.: US 12,196,210 B2
(45) Date of Patent: Jan. 14, 2025

(54) CENTRIFUGAL BLOOD PUMP WITH HYDRODYNAMIC BEARING

(71) Applicant: Abiomed Europe GmbH, Aachen (DE)

(72) Inventors: Thorsten Siess, Aachen (DE); Gerd Spanier, Aachen (DE)

(73) Assignee: Abiomed Europe GmbH, Aachen (DE)

( * ) Notice: Subject to any disclaimer, the term of this patent is extended or adjusted under 35 U.S.C. 154(b) by 46 days.

(21) Appl. No.: 17/355,880

(22) Filed: Jun. 23, 2021

(65) Prior Publication Data

US 2022/0042511 A1    Feb. 10, 2022

Related U.S. Application Data

(63) Continuation of application No. 14/433,135, filed as application No. PCT/EP2013/071273 on Oct. 11, 2013, now Pat. No. 11,092,158.

(30) Foreign Application Priority Data

Oct. 12, 2012 (EP) ..................................... 12188316

(51) Int. Cl.
*F04D 13/02* (2006.01)
*A61M 60/178* (2021.01)
(Continued)

(52) U.S. Cl.
CPC ......... *F04D 13/027* (2013.01); *A61M 60/178* (2021.01); *A61M 60/232* (2021.01);
(Continued)

(58) Field of Classification Search
CPC .......... F04D 13/027; F04D 1/00; F04D 13/06; F04D 29/186; F04D 29/426;
(Continued)

(56) References Cited

U.S. PATENT DOCUMENTS 2,384,251 A * 9/1945 Hill ...................... F04D 29/584
165/104.31
3,918,829 A * 11/1975 Korzec ................. F04D 29/448
415/207
(Continued)

FOREIGN PATENT DOCUMENTS

CN       101371041 A    2/2009
CN       202355626 U    8/2012
(Continued)

OTHER PUBLICATIONS

International Search Report for International Application No. PCT/EP2013/071273 dated Apr. 17, 2014.

*Primary Examiner* — Connor J Tremarche
(74) *Attorney, Agent, or Firm* — Botos Churchill IP Law LLP

(57) ABSTRACT

A centrifugal blood pump without a mechanical bearing comprises a pump casing (1), an impeller (9) arranged in the pump casing rotatably about the central axis and freely movable axially and radially within a limited clearance. The impeller has per-manent magnets or permanently magnetized magnetic regions (N/S) which cooperate with an electromagnetic drive to set the impeller rotating. A circular wall (12) or circularly arranged wall sections are provided within the pump casing, their inner surfaces defining a radial clearance together with the outer circumference of the impeller to form a hydrodynamic radial bearing for the impeller.

34 Claims, 10 Drawing Sheets

(51) Int. Cl.
  *A61M 60/232* (2021.01)
  *A61M 60/419* (2021.01)
  *A61M 60/585* (2021.01)
  *A61M 60/824* (2021.01)
  *A61M 60/873* (2021.01)
  *F04D 1/00* (2006.01)
  *F04D 7/04* (2006.01)
  *F04D 13/06* (2006.01)
  *F04D 29/18* (2006.01)
  *F04D 29/42* (2006.01)
  *H02K 1/2795* (2022.01)
  *H02K 3/47* (2006.01)
  *A61M 60/148* (2021.01)
  *A61M 60/422* (2021.01)

(52) U.S. Cl.
  CPC ........ *A61M 60/419* (2021.01); *A61M 60/585* (2021.01); *A61M 60/824* (2021.01); *A61M 60/873* (2021.01); *F04D 1/00* (2013.01); *F04D 7/04* (2013.01); *F04D 13/06* (2013.01); *F04D 29/186* (2013.01); *F04D 29/426* (2013.01); *H02K 1/2795* (2022.01); *H02K 3/47* (2013.01); *A61M 60/148* (2021.01); *A61M 60/422* (2021.01)

(58) Field of Classification Search
  CPC .............. A61M 60/419; A61M 60/824; A61M 60/178; A61M 60/873; A61M 60/148; A61M 60/422; H02K 3/47
  See application file for complete search history.

(56) References Cited

U.S. PATENT DOCUMENTS

| | | | | |
|---|---|---|---|---|
| 6,345,961 B1 * | 2/2002 | Oklejas, Jr. | ............ | F04D 29/448 417/407 |
| 6,421,239 B1 | 7/2002 | Huang | | |
| 6,623,475 B1 * | 9/2003 | Siess | ............ | F04D 13/026 417/420 |
| 2001/0002234 A1 * | 5/2001 | Woodard | ............ | F04D 29/181 415/182.1 |
| 2002/0094281 A1 * | 7/2002 | Khanwilkar | ........ | A61M 60/178 417/420 |
| 2002/0180285 A1 | 12/2002 | Machiroutu | | |
| 2002/0180825 A1 | 12/2002 | Buswell et al. | | |
| 2004/0143151 A1 * | 7/2004 | Mori | ............ | A61M 60/419 600/16 |
| 2004/0223872 A1 * | 11/2004 | Brian | ............ | A61M 1/267 604/6.14 |
| 2006/0133919 A1 * | 6/2006 | Dooley | ............ | F04D 29/181 415/75 |
| 2007/0297923 A1 | 12/2007 | Tada | | |
| 2008/0234623 A1 * | 9/2008 | Strauss | ............ | A61M 1/262 604/6.14 |
| 2009/0041595 A1 * | 2/2009 | Garzaniti | ............ | A61M 60/816 417/356 |
| 2009/0234447 A1 * | 9/2009 | LaRose | ............ | A61M 60/165 417/423.1 |
| 2011/0238172 A1 | 9/2011 | Akdis | | |
| 2012/0035411 A1 * | 2/2012 | LaRose | ............ | F04D 29/048 600/16 |
| 2012/0130152 A1 * | 5/2012 | Ozaki | ............ | F04D 29/048 600/16 |
| 2012/0253103 A1 | 10/2012 | Robert | | |

FOREIGN PATENT DOCUMENTS

| | | |
|---|---|---|
| CN | 102694444 A | 9/2012 |
| CN | 104703637 A | 6/2015 |
| EP | 1495773 A2 | 1/2005 |
| EP | 1598087 A2 | 11/2005 |
| JP | H09206372 A | 8/1997 |
| JP | 2002531184 A | 9/2002 |
| JP | 2002315824 A | 10/2002 |
| JP | 2002541986 A | 12/2002 |
| JP | 2005028137 A | 2/2005 |
| JP | 2005270345 A | 10/2005 |
| JP | 2005287598 A | 10/2005 |
| JP | 2007000350 A | 1/2007 |
| JP | 2007506027 A | 3/2007 |
| JP | 2013212218 A | 10/2013 |
| WO | 0064508 A1 | 11/2000 |
| WO | 2008136979 A1 | 11/2008 |
| WO | 2014057087 A1 | 4/2014 |

* cited by examiner

CENTRIFUGAL BLOOD PUMP WITH HYDRODYNAMIC BEARING

CROSS-REFERENCE TO RELATED APPLICATIONS

This application is a continuation of U.S. application Ser. No. 14/433,135, filed Apr. 2, 2015, now U.S. Pat. No. 11,092,158, which is a national phase entry under 35 U.S.C. § 371 of International Application No. PCT/EP2013/071273, filed Oct. 11, 2013, which claims priority to European Patent Application No. 12188316.9, filed Oct. 12, 2012, the disclosures of all of which are incorporated herein by reference in their entirety.

BACKGROUND OF THE INVENTION

The invention relates to a centrifugal blood pump, i.e. a pump having a rotating impeller by means of which blood is transported in an outward radial direction.

The blood pump is particularly suitable for long-term blood conveyance but may likewise be used only temporarily and offers a delivery rate of at least 4 and up to 10 liters per minute.

Centrifugal blood pumps for long-term use are described e.g. in U.S. Pat. No. 6,623,475 B1. In order to render the blood pump suitable for long-term use, mechanical bearings are omitted in this type of blood pump so as to avoid the danger of abrasive particles of the bearings contaminating the blood and further to prevent thrombosis from occurring at the bearings. In addition, bearing wear is commonly the most life-shortening parameter of a blood pump. Instead, the impeller of the pump is freely movable within a limited clearance in the pump casing. The impeller is rotated by means of an external electromagnetic drive cooperating with magnets provided on the blades of the impeller. Radial centering of the impeller results from the impeller magnets axially cooperating with the driving means. However, the magnetic forces of the impeller magnets tend to pull the impeller axially towards the electromagnetic drive and, thus, against the wall separating the drive from the impeller. In order to overcome such axial attraction forces, the impeller blades comprise supporting surfaces which hydrodynamically lift the impeller during rotation such that the impeller slides on a fluid cushion, i.e. a blood cushion, thus being kept at an axial distance from said wall. In this way, the impeller is centered in the pump casing both radially and axially without any bearing and without any impeller mounting shaft.

Blood pumps of the afore-described present type may be attached to the apex of the left ventricle. An outflow graft of the blood pump is attached to the ascending or descending aorta. Once in place, blood flows from the left ventricle through the blood pump into the aorta and circulates into the body. The pump is electrically driven and the drive line cable accesses the patient's skin and connects the implanted pump to an externally worn controller, which may be powered by batteries. The required power consumption lies below 10 W, preferably in the range of 6 W under physiologically relevant operating conditions, such that the pump has a long service life even when configured as a battery-operated portable device or when used with a wireless TET (transcutaneous energy transport) or TEIT (transcutaneous energy and information transport) device.

The poles of horse-shoe-like electromagnets of the electromagnetic drive are arranged outside the pump casing above and below the respective poles of the magnets of the impeller. Cyclically changing the poles of the electromagnets causes them to generate a rotating magnetic field carrying along the impeller. A maximum efficiency can be achieved with this type of electromagnetic drive when the change of the poles of the electromagnets is coordinated close to the breakdown torque, i.e. with a relatively large distance between the carrying electromagnets and the respectively carried magnets of the impeller. However, this has the adverse effect that the axial attracting forces between the electromagnets and the impeller magnets become relatively small so that the radial self-centering effect on the impeller is also small. Thus, in order to maintain a radial self-centering effect, the blood pump is not operated with its maximum efficiency.

In order to increase the torque on the prior art impeller, the strength of the impeller magnets, i.e. the amount of magnetic material on the impeller, could be increased, but this is limited due to the size and maximum weight of the blood pump, which, for the present invention, should not exceed a diameter of 40 mm and a height of 12 mm and which should weigh less than 50 grams, preferably less than 40 grams. In addition, the stronger the magnets are, the more difficult it is to get the pump started, because in the starting phase the magnets of the impeller cling to the horseshoe-like electromagnets of the electromagnetic drive means.

Alternatively, the energy supplied to the electromagnets could be increased. But this is difficult to achieve, because the energy consumption of the pump should be kept low at less than 10 W, preferably no more than 6 W, such that the pump has a long service life when configured as a battery-operated portable device or such that it can be driven by a TET or TEIT device.

There is thus the general problem of increasing the torque on the impeller of the blood pump while at the same time ensuring that the impeller remains axially and radially centered without any mechanical bearing.

A centrifugal blood pump of the general type as described above is known from HeartWare International Inc., Framingham, Massachusetts. The impeller is radially centered with passive magnetic forces using static magnets centrally arranged in the pump housing, on the one hand, and repelling magnets mounted on an inner circumference of the impeller, on the other hand. However, the provision of additional magnets for the radial centering of the impeller substantially adds to the overall weight of the pump. In addition, the repelling magnets of the impeller tend to be drawn axially towards the electromagnets of the drive means. Therefore, only a few starts are guaranteed with this pump. In addition, the axial magnetic forces are twice as high as the radial balancing forces. This massive axial force has to be levitated by the axial hydrodynamic lifting forces, which limits the pump's maximum rotational speed.

BRIEF SUMMARY OF THE INVENTION

It is therefore a primary object of the present invention to provide a centrifugal blood pump which has a low weight and can offer high torque on the impeller, wherein the impeller is axially and radially centered without any mechanical bearing. A secondary object of the present invention is to provide a centrifugal blood pump with reduced frictional forces at the time when the pump is started.

The primary object is achieved according to the present invention by a centrifugal blood pump with the features of independent claim 1. Preferred embodiments and further developments of the invention are specified in the claims dependent thereon.

The centrifugal blood pump of the present invention without a mechanical bearing has a pump casing with a central axis, a blood flow inlet disposed along said central axis and a blood flow outlet disposed on a circumference of the pump casing, as is generally known e.g. from U.S. Pat. No. 6,623,475 B1. Furthermore, the centrifugal blood pump has an impeller that is rotatably arranged about said central axis in the pump casing and has radially extending blades defining passages therebetween for radial blood flow. The impeller is freely movable both axially and radially within a limited axial clearance and a limited radial clearance. The impeller is provided with permanent magnets or permanently magnetized magnetic regions which cooperate with an electromagnetic drive such that the impeller can be set rotating about said central axis, as is also generally known from U.S. Pat. No. 6,623,475 B1. According to the invention, the radial clearance within which the impeller is freely movable is defined by an outer circumference of the impeller and an inner surface of a circular wall or plurality of wall sections arranged in a circle about the central axis within the pump casing. The radial clearance is 100 µm or less, so as to provide a hydrodynamic radial bearing for the impeller in the pump casing. Preferably, the radial clearance is 50 µm or less. With a clearance of about 50 µm, a constant lifting force can be guaranteed while allowing for sufficient blood to pass through the narrow gap to wash all pump and impeller surfaces. The hydrodynamic radial bearing makes it possible to dispense with any mechanical radial bearing and further makes it possible to dispense with or at least reduce the size of a static magnetic radial bearing.

The radial clearance between the impeller and the wall or wall sections preferably comprises a plurality of sections in which the clearance converges radially, when seen in the direction of rotation of the impeller. In other words, in these sections the gap defined by the radial clearance between the impeller and the wall or wall sections becomes smaller in a circumferential direction. As a result, upon rotation of the impeller, blood is transported into the clearance and, due to the clearance converging in the direction of rotation of the impeller, tends to urge the impeller away from the wall or wall sections, thereby contributing to the radial centering of the impeller about the central axis of the pump casing while minimizing the time during which the blood components are exposed to significant shear forces.

The converging sections can be realized by providing corresponding recesses in the radially inner surface of the wall or wall sections or by providing the outer circumferential surface of the impeller with respective recesses or ramps, or by a combination of recesses or ramps on the outer circumferential surface of the impeller and radially inner surface of the wall or wall sections.

In order to prevent the impeller from axially clinging to an adjacent wall due to attracting forces acting between the permanent magnets of the impeller and the electromagnets, it is preferably provided to construct the electromagnetic drive with coils having no ferromagnetic core. In this situation, for the coils to generate the necessary magnetic fields that are usually provided by the ferromagnetic cores penetrating the prior art coils, the coils (without a core) are arranged in a plane axially spaced from the impeller, namely immediately above or below or, preferably, above and below the impeller magnets, at a minimum distance. For instance, the wall separating the coils from the impeller may consist of a 100 µm thick, or even thinner, ceramic plate. Without the ferromagnetic core, the magnets of the impeller are not magnetically attracted to the electromagnetic drive when the electromagnetic drive is not in operation. This substantially reduces the friction between the impeller and the axially adjacent walls, not only at the time when the impeller is set rotating but also during its operation, since the two sets of electromagnetic drive coils are perfectly mirror imaged on both sides of the impeller and, as such, balance the axial forces. Accordingly, the magnets on the impeller may be made stronger as compared to the prior art impeller magnets, thereby further increasing the maximum possible torque that can be imposed on the impeller by the electromagnetic drive.

The thickness of the ceramic plate is chosen such that it does not severely affect the magnetic field created by the coils, but is sufficiently strong to withstand sliding contact with the impeller. Accordingly, a preferred thickness of the ceramic plate is within the range of 50 to 150 µm, preferably 80 to 120 µm, more preferably about 100 µm.

The coils are preferably potted in a polymer matrix to stabilize them and protect them from corrosion. It is preferred to mount the coils preferably directly, or alternatively indirectly, on the aforementioned ceramic disc, which limits the axial movement of the impeller, so that the coil and the ceramic disc form an integral component. The polymeric material in which the coils are potted can be cast directly on the ceramic disc.

The coils preferably have a non-circular axial cross section, more preferably a substantially oval or trapezoidal one, so as to better fill the available space or, in other words, so as to increase the overall axial cross section of the set of coils. Due to the increased coil cross sections, stronger magnetic fields can be created and, thus, the torque on the impeller can be increased.

In some embodiments of the invention, the radially outer surface of the impeller blades, together with the circular wall or circularly arranged wall sections, may define the hydrodynamic radial clearance. In these cases it is advantageous when the radially outer surfaces of the impeller blades cover a large part of the impeller's outer circumference. Thus, the circumferential dimension of at least one or all of the impeller blades preferably increases radially, so that an axial cross section of the impeller may roughly have a triangular or trapezoidal form. As stated above, the radially outer surfaces of the impeller blades may have recesses which, together with the inner surface of the circular wall or circularly arranged wall sections, form converging sections into which blood is transported upon rotation of the impeller so as to urge the impeller away from the wall or wall sections.

It is further advantageous if an impeller blade has a leading surface, as seen in the direction of rotation of the impeller, which is convex with respect to the blade's radial extension. This design supports the radial centering of the impeller and offers a more laminar blood flow as compared to an impeller with straight or concave blades. It further provides a higher primary pressure increase within the impeller.

It has been found to be particularly advantageous if the aspect ratio (i.e., the ratio of the diameter versus the height) of the impeller is 4:1 or more, preferably 6:1 or more. The higher the aspect ratio is, the more stable the impeller is with respect to wobbling about the axis of rotation.

It is further generally advantageous if the radial blood flow passages defined between the impeller blades are relatively wide. Therefore, instead of providing each impeller with one magnet or one magnetic region, it is preferable to combine two magnets or magnetic regions in one impeller blade. In this way, the number of impeller blades can be halved, thereby doubling the width of the impeller blades as well as the width of the blood blow passages therebetween. Accordingly, in a preferred embodiment, a first magnet or magnetic region and a second magnet or magnetic region, each having a north pole and a south pole, are combined in one impeller blade, with the north and south poles of the first magnet or magnetic region being arranged upside down with respect to the north and south poles of the second magnet or magnetic region.

Since the blood pump according to the invention is designed for long-term use, the magnetic material of the impeller must be protected from corrosion caused by the contact with blood. Therefore, the magnets or magnetic regions of the impeller are preferably covered all over with metal, such as titanium or a biocompatible precious metal. The thickness thereof is preferably no more than 50 µm, more preferably no more than 20 µm, in order not to inordinately reduce the effectiveness of the magnet.

If a circular wall is provided within the pump casing to define the hydrodynamic radial clearance together with the outer circumference of the impeller, such wall preferably has a plurality of circumferentially spaced through openings for blood to flow from the impeller towards the pump casing's blood flow outlet. In one embodiment, however, the circular wall can be subdivided into two circular rings on each side of the rotor, which eliminates the need for such openings and leads to a 360° ring-like opening. The 360° through flow opening can in addition—depending on the wall thickness of the two circular wall rings—serve as a first diffuser providing a first pressure increase. Likewise, the circumferentially spaced through openings can serve as a first diffuser. Such through openings are not needed where the circular wall is replaced with wall sections arranged in a circle about the central axis of the pump casing, because in this case the through openings are formed by the gaps between neighboring wall sections.

In case the wall thickness is used to provide a first diffuser, the wall thickness is preferably at least 2 mm. Preferably, the cross-section of the ring-like opening or the spaced apart opening increases in a radially outward direction, wherein the opening angle of the opening or openings preferably does not exceed 7°. Greater opening angles would cause a detachment of the flow and lead to undesired turbulences. The openings may be equal along the circumference of the circular wall and/or the wall thickness may be constant. In an embodiment the height, width and/or diameter of the openings may be different and/or the wall thickness (i.e. the length of the openings) may vary along the circumference of the circular wall. This means that the deceleration of the blood in the first diffuser may either be constant or may vary along the circumference of the circular wall. This way, by means of the first diffuser a constant pressure along the circumference of the impeller can be achieved such that the radial hydrodynamic bearing is stable and does not oscillate or vibrate due to pressure variations at the pump inlet. Although a diffuser effect could also be achieved by increasing the diameter of the impeller, such that the passages serve as a diffuser, it is preferred to provide the diffuser in the circular wall or wall sections because a greater diameter of the impeller leads to greater shear forces at the outer circumference of the impeller.

In order to avoid pulsation of the blood flow, caused by the blood flowing from the impeller through the circular wall or circularly arranged wall sections towards the pump casing's blood flow outlet, all distances between adjacent through openings in the wall or wall sections are made smaller than all distances between the radially outer ends of the impeller blades. Accordingly, a passage defined between two adjacent impeller blades is always open to at least one through opening provided in the circular wall or circularly arranged wall sections.

A ring diffuser is preferably provided peripherally of the circularly arranged wall or wall sections, and the blood flow outlet of the pump casing is preferably tangentially disposed on the pump casing's circumference, i.e. the ring diffuser preferably ends in a tangential outlet. The cross section of the ring diffuser preferably increases linearly or exponentially along its circumferential direction. Alternatively, the ring diffuser may have a constant cross section.

The invention will be described in further detail in relation to two preferred embodiments and some variants thereof. According to the first embodiment, the impeller comprises a first disc and a second disc which are axially spaced apart. Each disc has magnetic regions and a central opening arranged for axial blood flow centrally through the discs, such as axial blood inflow through the first disc and axial blood outflow through the second disc, or axial blood inflow through both the first and second discs. In this first embodiment, the blades of the impeller are arranged between the two magnetic discs so that blood flows mainly radially between the two discs through the passages defined by the blades.

However, a small part of the blood flows above and below the plates so that the impeller is hydrodynamically supported on both axial sides thereof and thorough washing of all surfaces is guaranteed. The blood flow above and below the two discs is relatively low, but sufficient to keep the impeller axially spaced apart from the pump housing. The respective surfaces of the discs are preferably planar and the respectively adjacent walls, such as the aforementioned ceramic plates, are preferably likewise planar so that the blood flows between the planar disc surfaces and the adjacent planar walls. Thus, the overall construction is relatively simple.

However, the hydrodynamic lifting effect may be increased if one or both of the disc surfaces and/or one or both of the adjacent walls provides ramps extending about the central axis in a circumferential direction.

The radially outer circumference of the first and second magnetic discs of the impeller is preferably circular and forms at least a part or all of the radially outermost circumference of the impeller which, together with the inner surface of the wall or plurality of wall sections, defines the radial clearance forming the hydrodynamic radial bearing for the impeller. As mentioned above, in the case that the outer circumference of the first and second discs are the sole impeller portions contributing to the hydrodynamic radial bearing for the impeller, the plurality of wall sections may comprise an upper circular wall section and a lower circular wall section which are axially spaced apart so as to form one continuous circumferential through opening for blood flow from the impeller towards the blood flow outlet of the pump casing. Thus, any wall sections blocking or hindering the blood which leaves the impeller radially can be omitted. As a result, the blood flow is more laminar and blood damage is reduced.

However, where the wall or plurality of wall sections provide a plurality of circumferentially spaced through openings for blood to flow from the impeller towards the blood flow outlet, as explained above, all distances between two adjacent through openings are preferably smaller than all distances between the radially outer ends of the impeller blades, in order to avoid pulsation of the blood flow. In this way, all of the radial blood flow passages defined between the impeller blades are always in flow communication with the outflow opening of the pump casing.

According to a variant of the first embodiment, the first and second discs do not form an outer circumference of the impeller, but rather one or both of the first and second discs are circumferentially surrounded by a circular rim which axially extends from the axial side or sides of the impeller blades and integrally interconnects the blades. In this variant, the circular rim forms a part or all of the radially outermost circumference of the impeller and assumes the same hydrodynamic bearing function that has been explained above in respect of the variant where the outer circumference of the first and/or second magnetic discs contributes to the hydrodynamic radial bearing of the impeller.

It is preferable in this variant of the first embodiment as well as in other variants of this and all other embodiments of the invention to form all blades of the impeller together as an integral injection molded piece, except in the case where the blades are formed entirely from magnetic material.

The second embodiment differs from the first embodiment in that the impeller comprises only one disc rather than two discs. The single disc has a central opening arranged for axial blood flow through the disc, and the impeller blades are arranged on the disc so as to extend axially from both axial sides of the disc. In this second embodiment, the impeller blades are either formed as magnets, i.e. they are entirely formed from magnetic material, or have magnetic regions. This is important because the disc is centrally arranged within the impeller and, therefore, relatively far away from the coils of the magnetic drive. The disc can therefore contribute only little to the maximum torque achievable with the blood pump, even if it is made from magnetic material. Nevertheless, according to one variant of the second embodiment, both the disc and the blades may be made of ferromagnetic metal. The ferromagnetic metal is permanently magnetized so that alternating magnetic regions are provided, preferably without interruption, along the entire circumference of the impeller. It is even possible and further preferable in this variant to form the disc and the blades as an integral piece of ferromagnetic metal, said piece, including the disc, being magnetized.

Since a disc made of metal substantially adds to the overall weight of the blood pump, another preferred variant of the second embodiment provides for the disc comprising or being entirely made of polymer material. The overall weight of the blood pump can thus be reduced.

According to another variant of the second embodiment, the disc and the impeller blades may be composed as two semi-shells, within which the magnets are housed. The shells may be injection molded.

In this second embodiment, the circular wall or circularly arranged wall sections may also provide a plurality of circumferentially spaced apart through openings for blood to flow from the impeller towards the blood flow outlet, whereby, as explained, all distances between two adjacent through openings are preferably smaller than all distances between radially outer ends of the impeller blades, in order to prevent pulsation of the blood flow.

However, in a variant, the wall may extend radially inward so as to form, together with the circular radially outer surface of the impeller disc, the hydrodynamic radial bearing for the impeller. Accordingly, the blood may leave the impeller towards the pump casing's blood flow outlet partially above the radially extending wall and partially below the radially extending wall without any wall sections blocking or hindering such blood flow.

In the second embodiment, similarly to the prior art blood pump disclosed in U.S. Pat. No. 6,623,475 B1, a hydrodynamic bearing is provided for axially mounting the impeller so as to lift the impeller from the adjacent wall or walls, such as the afore-mentioned ceramic plate, upon rotation of the impeller. Accordingly, the impeller blades have upper and lower surfaces, whereby one or both of the upper and lower surfaces, together with the respective adjacent wall, define an axial clearance having sections in which the clearance converges in a circumferential direction. More specifically, the upper and lower surfaces provide ramps extending about the central axis in a circumferential direction so as to create a hydrodynamic axial force on the impeller. The ramp of one or more of the upper and lower surfaces may be formed as a curved or tapered leading edge of the respective blade, as seen in the direction of rotation of the impeller, passing into a straight section, which may be horizontal, i.e. perpendicular to the central axis, or inclined.

BRIEF DESCRIPTION OF THE DRAWINGS

Preferred embodiments of the invention will hereinafter be described in more detail with reference to the accompanying drawings, in which.

DETAILED DESCRIPTION OF PREFERRED EMBODIMENTS

Figure 1:
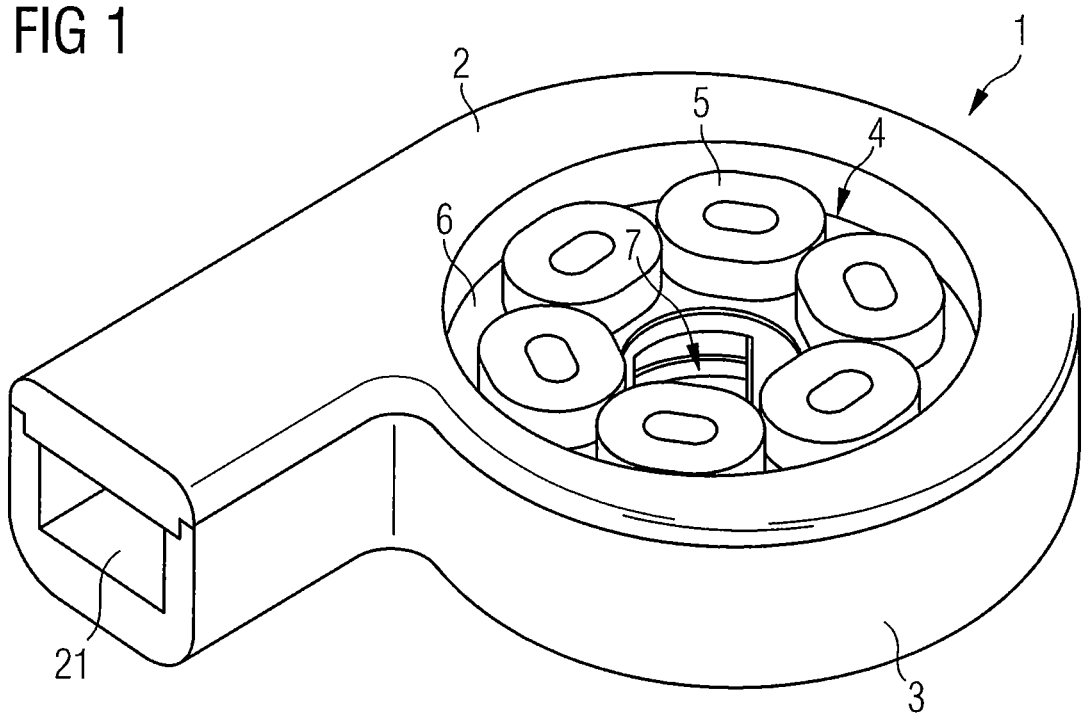
FIG. 1 shows a perspective view of a blood pump according to a first embodiment of the invention.

FIG. 1 shows a first embodiment of a centrifugal blood pump with a casing 1 comprising an upper shell 2 and a lower shell 3. The upper shell 2 as well as the lower shell 3 each have a circular recess 4 accommodating a set of six electromagnetic coils 5 therein. The number of coils can be different and is preferably dividable by three. The coils 5 do not have any ferromagnetic core. Preferably, they have an oval shape and may alternatively have a trapezoidal shape, so as to fully exploit the available space within the recess 4. The coils 5 are encapsulated in a polymer matrix directly on a very thin circular ceramic plate 6 having a thickness of only about 100 μm. The ceramic plate 6 has a central hole 7 constituting a blood flow inlet through which blood can enter the blood pump when the blood pump is appropriately connected e.g. to the apex of the left ventricle. The blood will exit the blood pump through the blood flow outlet 21. The ceramic plate 6 with the electromagnetic coils 5 mounted thereon together form a unitary coil assembly.

Figure 2:
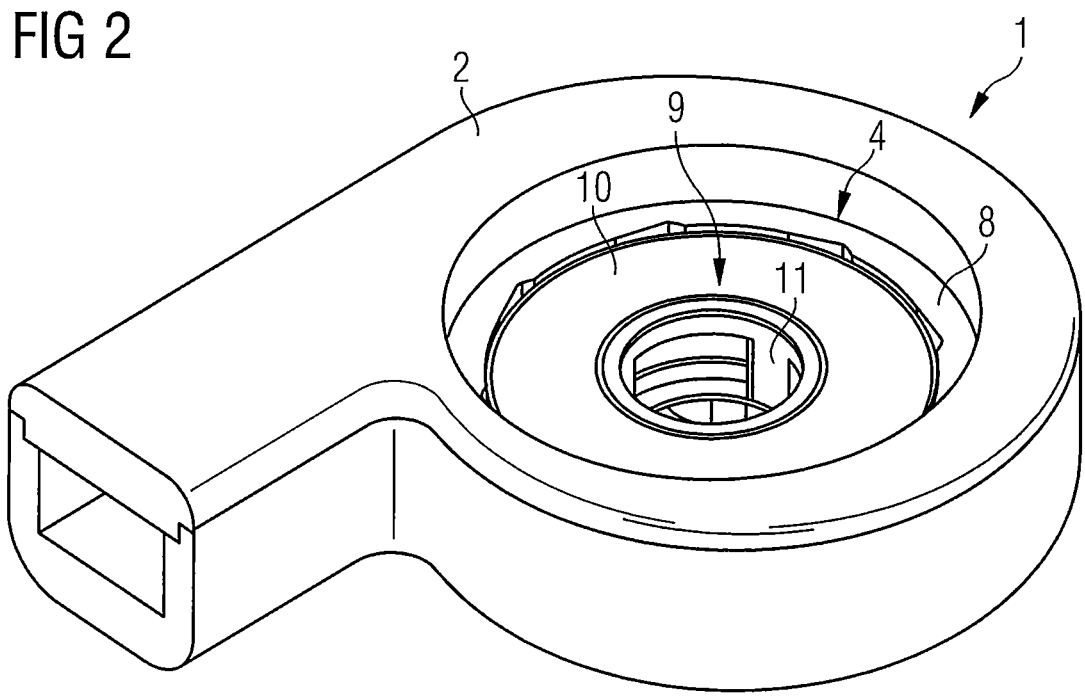
FIG. 2 shows the blood pump as shown in FIG. 1 without the upper set of electromagnetic coils and the planar ceramic surface.

FIG. 2 shows the blood pump of FIG. 1 without the coil assembly 5, 6. As can be seen, the recess 4 in the upper shell 2 of the pump casing 1 has a ledge 8 on which the ceramic plate 6 rests. The ledge 8 defines a step or further recess within the recess 4, within which the impeller 9 is accommodated so that it can rotate about a central axis of the pump casing 1. The impeller 9 comprises an upper magnetic disc 10 and a lower magnetic disc (not shown) and further a blade rotor 11 sandwiched between the two magnetic discs 10. The upper and lower surfaces of the impeller 9 and the axially inner surfaces of the upper and lower ceramic plates 6 of the two coil assemblies define a limited axial clearance within which the impeller 9 is freely axially movable. The radially outer circumference of the impeller 9 together with the lower inner surface of the stepped recess 4 define a radial clearance within which the impeller 9 is freely radially movable.

Figure 3:
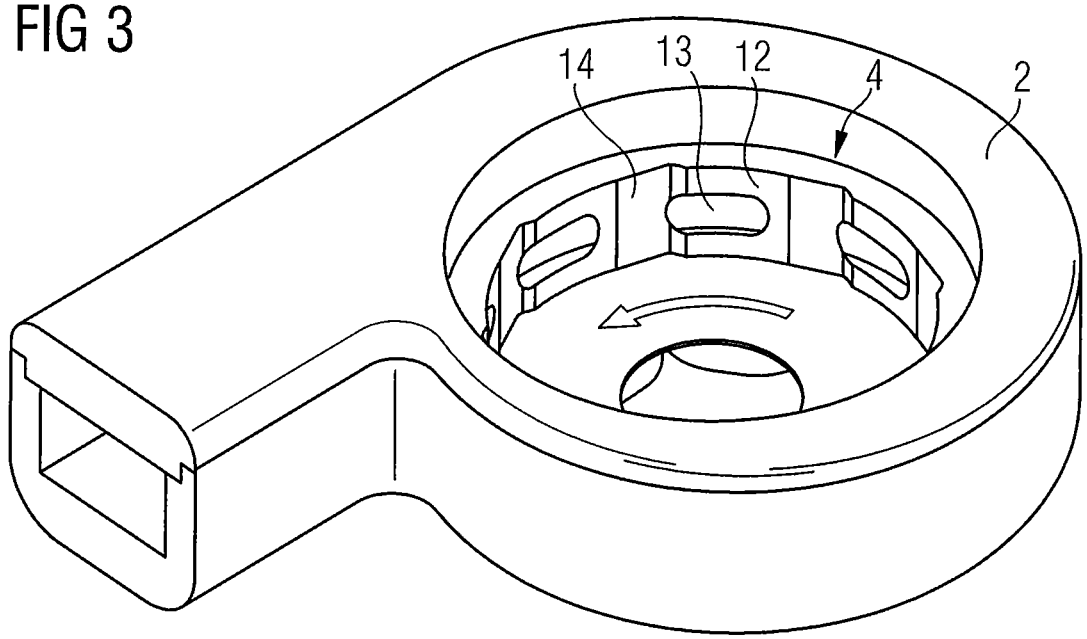
FIG. 3 shows the blood pump as shown in FIG. 2 without the impeller.

The lower wall 12 of the recess 4 limiting the radial clearance for the impeller 9 can be seen better in FIG. 3. The wall 12 is free-standing and has through openings 13 through which blood being radially propelled by the impeller can pass into a ring diffuser 20 (FIG. 4) arranged peripherally of the wall 12. Instead of the wall 12 having through openings 13, the wall may alternatively be composed of axially extending, spaced apart wall sections providing through openings therebetween.

The wall 12 is further provided with pockets 14 which are configured to enhance a hydrodynamic radial bearing effect on the impeller 9, when the impeller rotates about the pump casing's central axis. In the wall sections of the pockets 14, the radial clearance defined between the impeller's 9 outer circumference and the inner surface of the wall 12 radially converges, as seen in the direction of rotation of the impeller, which is indicated in FIG. 3 by an arrow.

Figure 4:
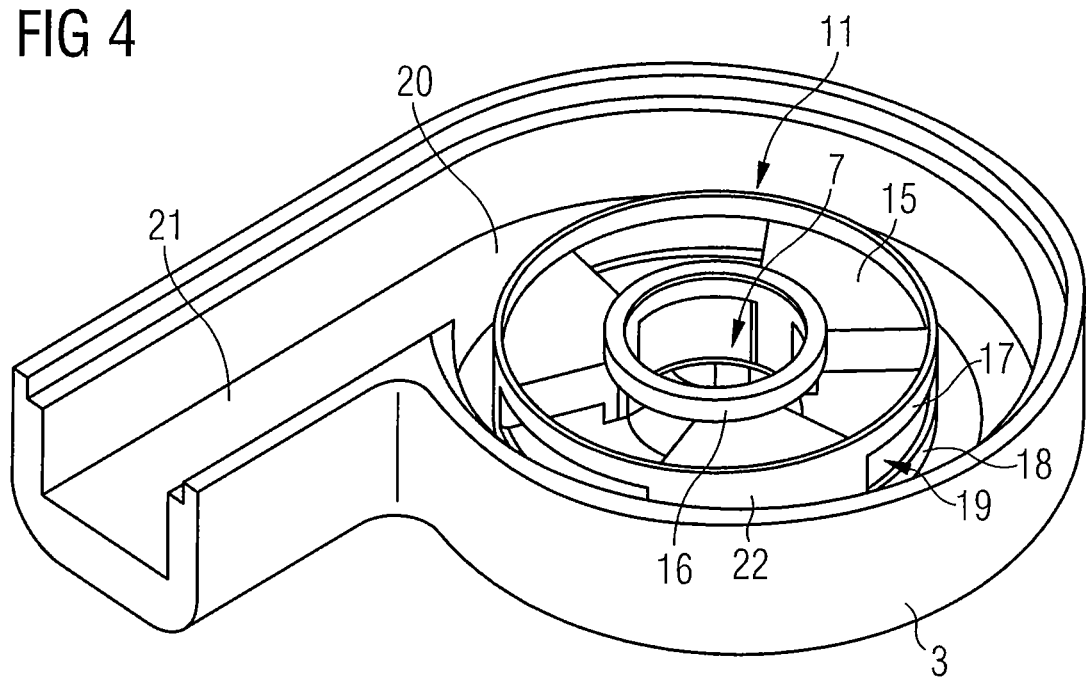
FIG. 4 shows the blood pump as shown in FIG. 2 without the upper pump housing shell and without the upper magnetic disc of the impeller.

FIG. 4 shows the lower shell 3 with the blade rotor 11, the upper and lower magnetic discs 10 of the impeller 9 being removed. As can be seen, the blade rotor 11 has three radially extending blades 15 held together by a central circular ring 16 and two upper and lower circumferential rings 17, 18. Passages 19 are defined between the blades 15 for blood to flow radially from a blood flow inlet, corresponding to the central hole 7, to the ring diffuser 20 arranged peripherally of the blade rotor 11 and further to a blood flow outlet 21 of the pump casing. Upon rotation of the impeller 9, the upper and lower circumferential rings 17, 18 will slide along the wall 12, namely above and below the wall's 12 through openings 13, whereas the radially outer surfaces 22 of the blade 15 and the passages 19 defined there-between will pass along the through openings 13 of the wall 12 (see FIG. 3). The distances between two adjacent through openings 13 in the wall 12 (or between corresponding axially extending wall sections) are dimensioned so that they are smaller than all distances between the radially outer ends of the blades 15 of the blade rotor 11. In this way, pulsation of the blood flow through the impeller 9 can be avoided, as the blood flow passages of the impeller are always open in a radially outward direction.

Figure 5:
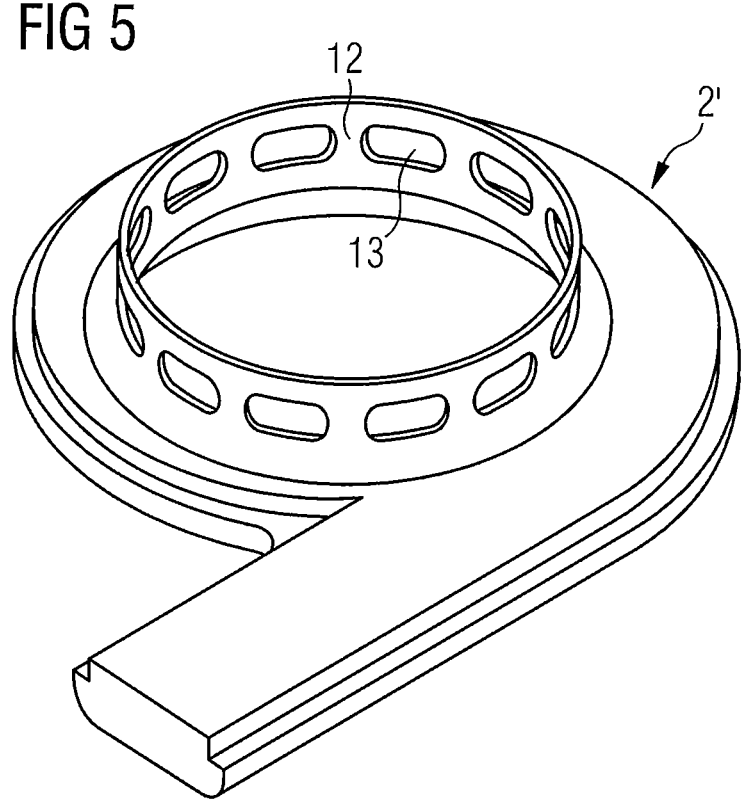
FIG. 5 shows an alternative upper pump housing shell upside down, having a wall without hydrodynamic pockets.

FIG. 5 shows an alternative upper shell 2' which differs from the upper shell 2 in FIG. 3 in that it has a larger number of through openings 13 and, more importantly, the inner surface of the wall 12 lacks pockets 14. A hydrodynamic radial bearing will nevertheless be established once the impeller 9 is set rotating. Alternatively (not shown), the wall 12 may be divided into an upper circular wall section forming part of the upper shell 2 and a lower circular wall section of the lower shell 3, each wall section preferably being provided with the afore-mentioned pockets 14, a continuous circular through opening 13 being formed between the two circular wall sections.

Figure 6:
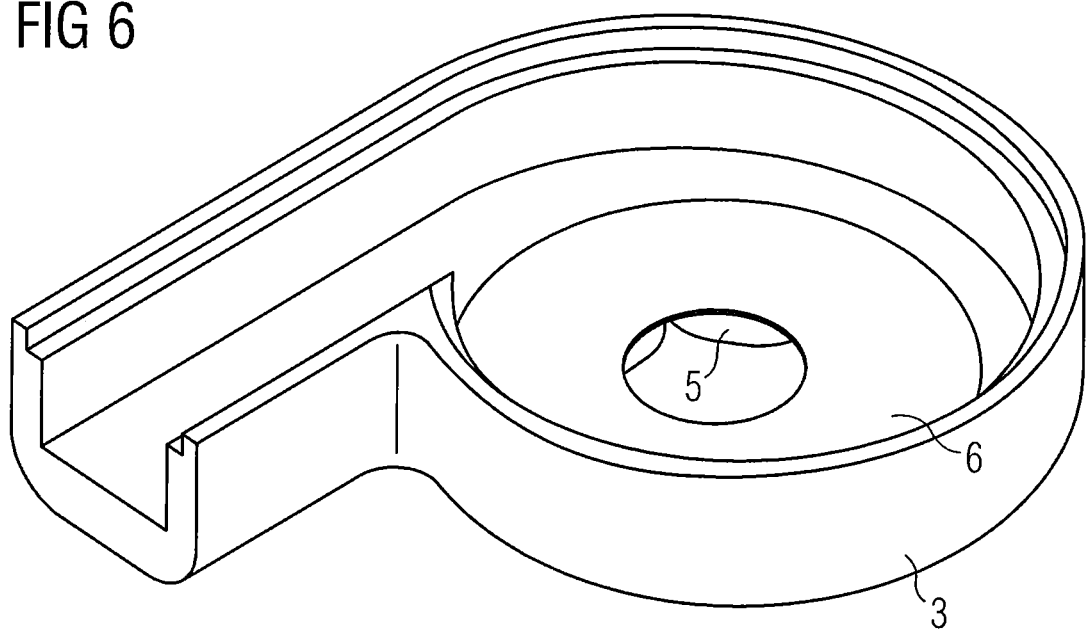
FIG. 6 shows the lower pump housing shell of the blood pump with the lower set of electromagnetic coils arranged on a thin ceramic disc.

FIG. 6 shows the lower shell 3 of the pump casing 1 with only the lower coil assembly 5, 6 positioned in a recess (not shown) of the lower shell 3. The central opening 7 in the coil assembly 5, 6 can be provided on one or both coil assemblies, thus allowing axial blood inflow from only one side or on both sides of the impeller.

Figure 7:
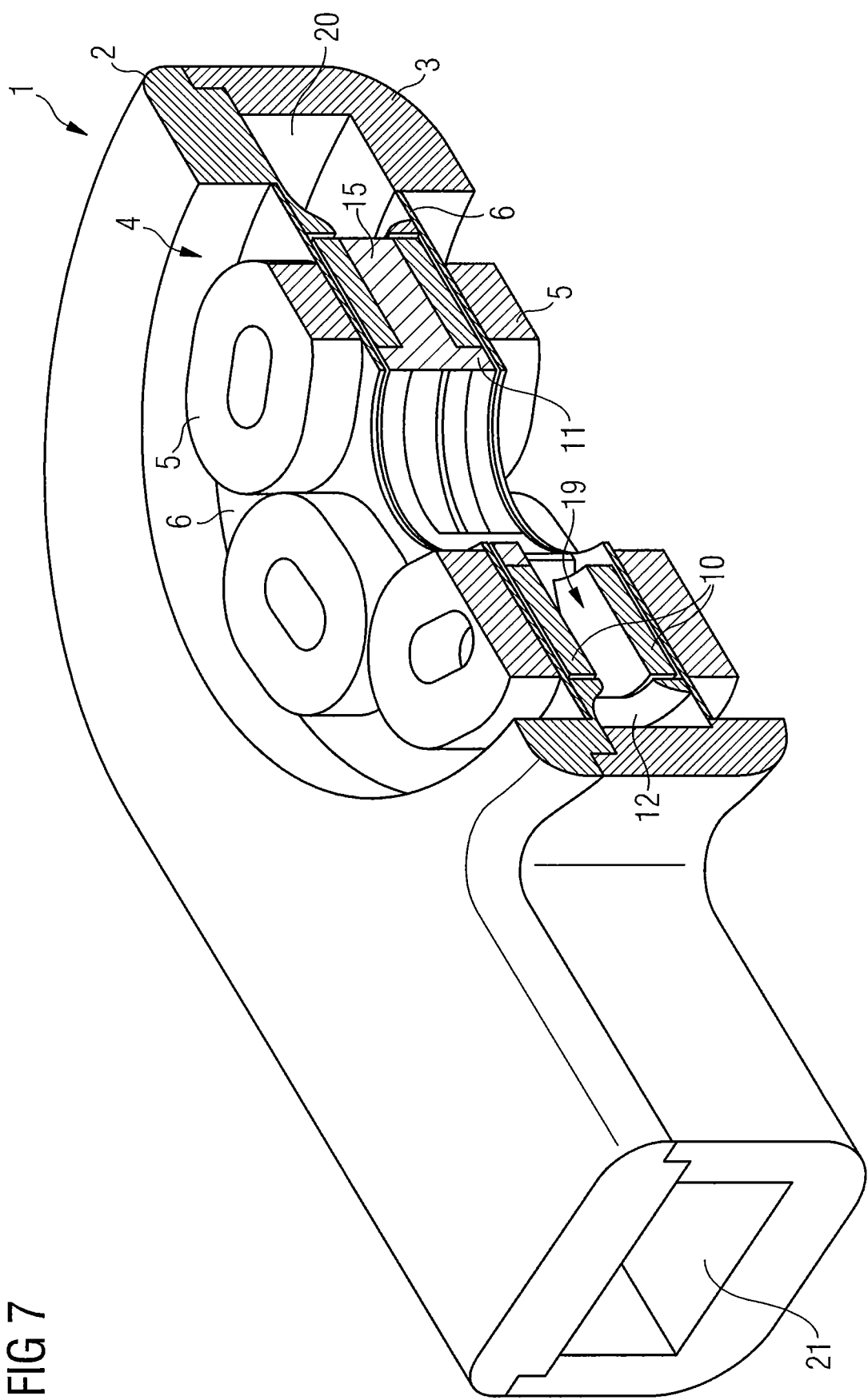
FIG. 7 shows a cross sectional view of the blood pump of FIG. 1.

FIG. 7 shows a cross-sectional view of the blood pump described above with all elements accordingly numbered. As can be seen, the upper and lower coil assemblies 5, 6 are identical in size and structure. The lower ceramic plate 6 can be supported on the free end of the wall 12 of the upper shell 2. The blade rotor 11 of the impeller 9 carrying a magnetic disc 10 on each side, as shown in the cross-sectional view in FIG. 7, is cut at one side through a blade 15 and at the other side through a passage 19 defined between two blades 15. As further becomes apparent from the cross-sectional view in FIG. 7, the cross section of the ring diffuser 20 increases in the circumferential direction of the blood pump in this embodiment.

Upon rotation of the impeller 9, blood flows radially through the passages 19 and also above and below the impeller's 9 magnetic discs 10 between the discs 10 and the ceramic plates 6. Their mutual contact surfaces are planar. Alternatively, one or both of these surfaces may have ramps extending in a circumferential direction so as to create a hydrodynamic lifting effect on the impeller. Although the lower ceramic plate 6 is shown as having a central hole, similar to the central hole 7 of the upper ceramic plate 6, the lower ceramic plate 6 preferably has no central hole but completely seals against blood leakage.

Figure 8:
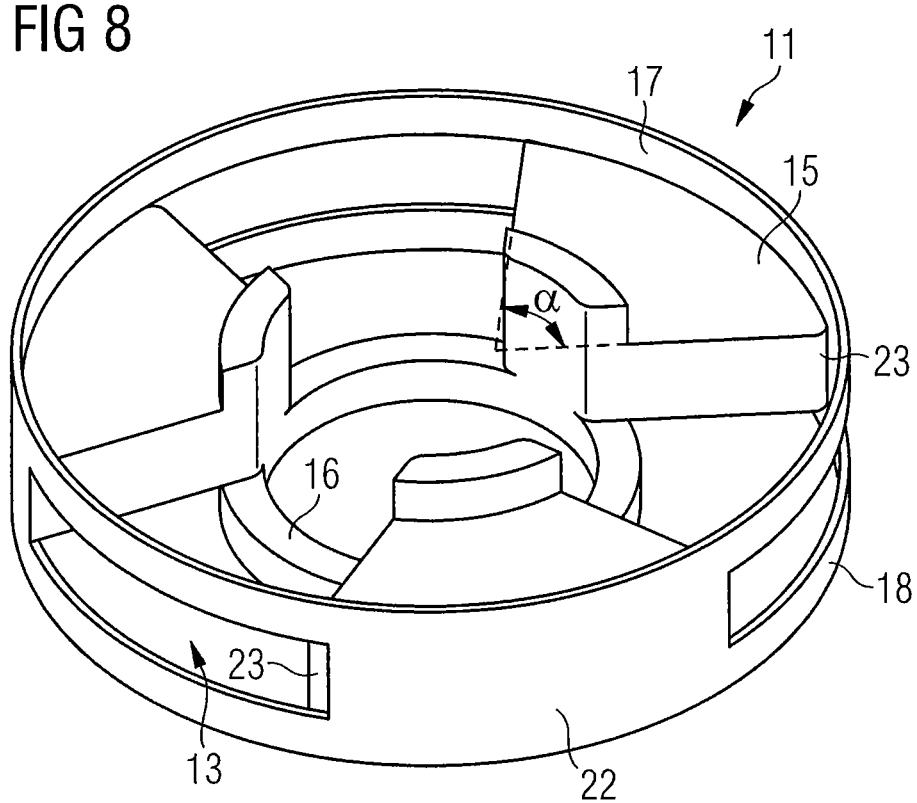
FIG. 8 shows the blade rotor of the impeller of the blood pump of FIG. 1.

FIG. 8 shows the blade rotor 11 separately, including the blades 15 and their radially outer surfaces 22, the through openings 13 defined between the blades 15, the central circular ring 16 as well as the upper and lower circumferential outer rings 17 and 18 connecting the blades 15 to form an integral piece, which is preferably injection molded. The blades 15 of the impeller 9 have an axially extending leading edge 23, as seen in the direction of rotation of the impeller, which is curved or tapered in order to enhance the hydrodynamic effect of the radially outer surfaces 22 and reduce blood damage. The number of blades 15 can be more than three, e.g. four, five or six. Likewise, the angular extension a of the blades may be larger or smaller than shown in FIG. 8. Also, the inner diameter of the blades may be larger or smaller than shown in FIG. 8.

Figure 9:
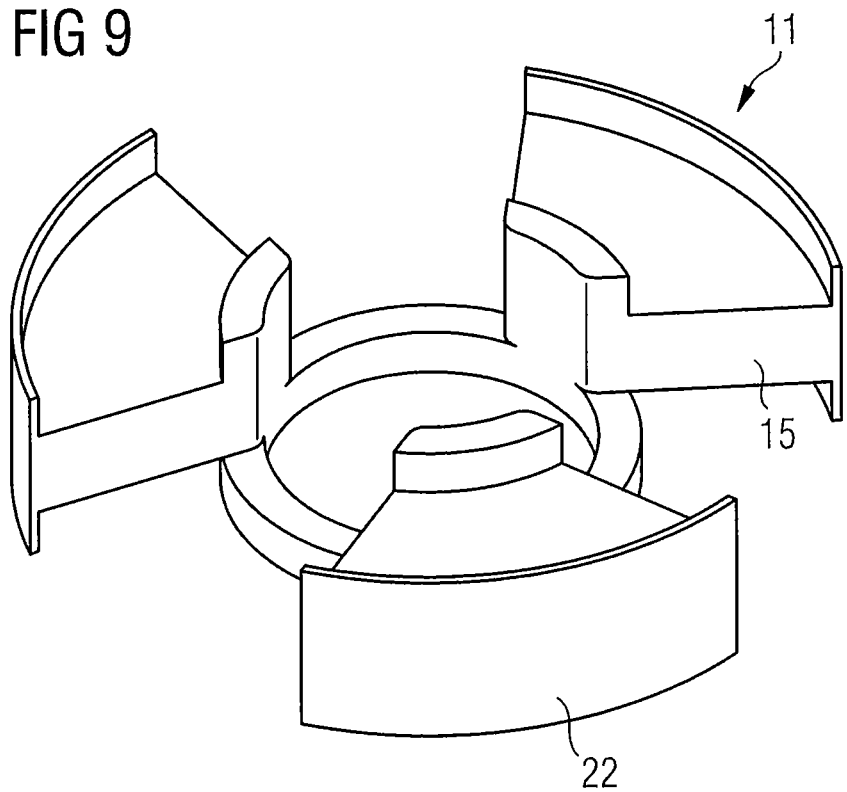
FIG. 9 shows a first alternative blade rotor.
Figure 10:
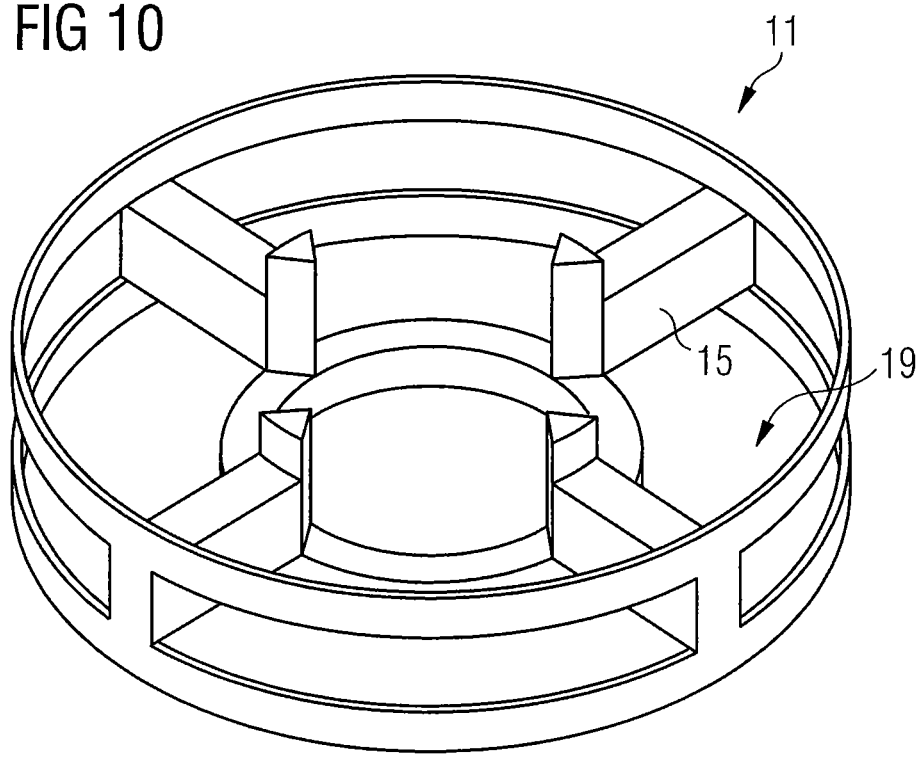
FIG. 10 shows a second alternative blade rotor.
Figure 11:
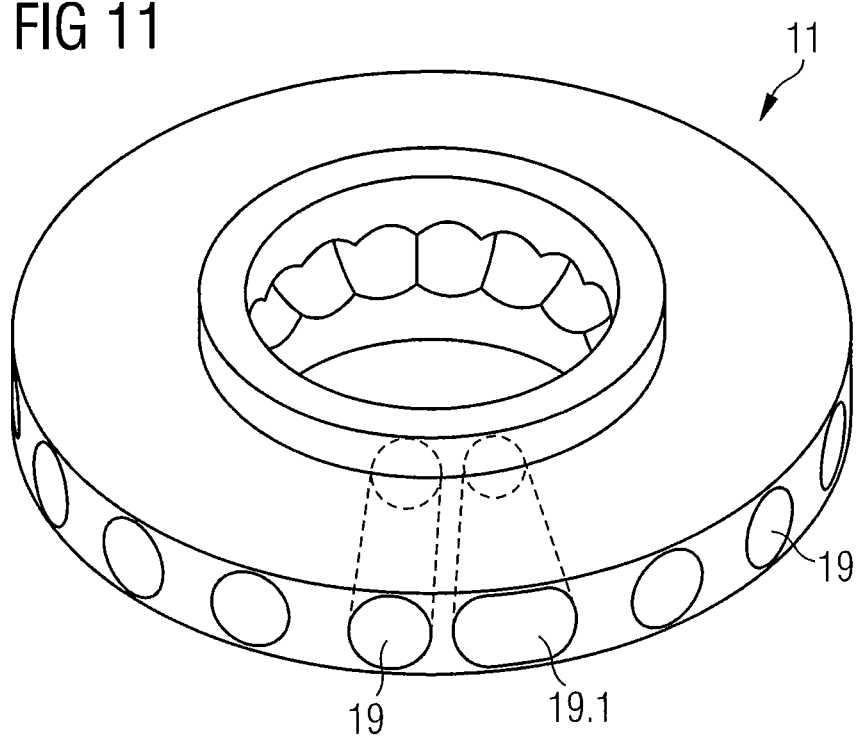
FIG. 11 shows a third alternative blade rotor.

FIGS. 9, 10 and 11 show a first, a second and a third variant of the blade rotor 11. The blade rotor 11 in FIG. 9 differs from the blade rotor 11 in FIG. 8 in that the upper and lower circumferential rings 17, 18 are interrupted. The hydrodynamic radial bearing for the impeller 9 is achieved with this variant of the blade rotor 11 mainly by the radially outer surfaces 22 of the blades 15. Alternatively, the magnetic disc 10 (not shown in FIG. 9) may be formed such that it fills the space of the missing sections of the upper and lower circumferential rings 17, 18. Here, too, it is advantageous if the blades 15 of the impeller have an axially extending leading edge, as seen in the direction of rotation of the impeller, which is curved or tapered in order to increase the hydrodynamic effect for the hydrodynamic radial bearing of the impeller and in order to reduce blood damage.

FIG. 10 shows a second variant of the blade rotor 11 in which the blades 15 are formed as straight bars, so that the passages 19 defined between adjacent blades 15 are accordingly increased.

The blade rotor 11 in FIG. 11 is formed from a polymeric washer-like disc having a number of radially extending passages 19 which may overlap in a central area of the blade rotor 11. The radial passages 19 may have a constant cross section or, as shown at 19.1, may have a cross section which increases towards the outer circumference.

In the embodiments described so far and in all variants thereof, the magnetic discs 10 are magnetized in sections in opposite directions. Each section has a first pole at the upper side of the disc and the respective opposite pole on the lower side of the disc. The number of magnetized sections is preferably eight but may likewise be four or twelve and should be different from the number of coils 5. Furthermore, instead of the upper and lower circumferential rings 17, 18, the radial dimensions of the circular magnetic discs 10 may be such that the outer circumferential radial surfaces of the magnetic discs replace the upper and lower circumferential rings 17, 18. In this case, the blades 15 are interconnected only by the central circular ring 16. The advantage is that more magnetic material is present, so that the maximum torque provided by the impeller may accordingly be increased.

Figure 12:
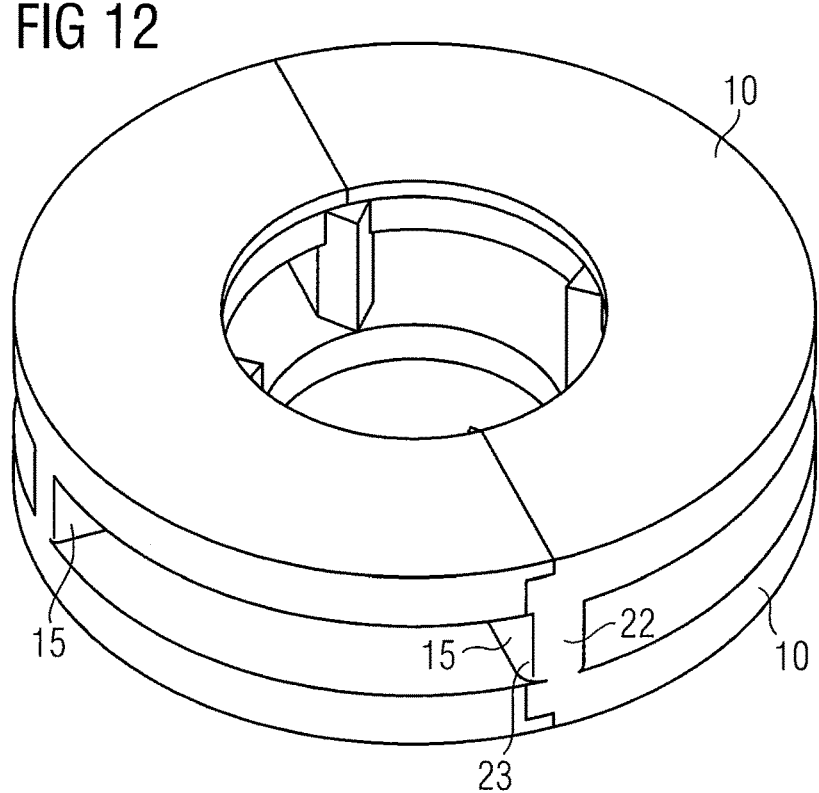
FIG. 12 shows an alternative impeller for the blood pump of FIG. 1 entirely made of ferromagnetic material, FIG. 13 schematically shows top views of various blade rotor forms.

FIG. 12 shows a further variant of an impeller that can be used in connection with the blood pump according to the first embodiment. Here the impeller is entirely made from permanently magnetized ferromagnetic material, i.e. not only the upper and lower magnetic discs 10 but also the radially extending blades 15 are magnetic. Again, the blades 15 have an axially extending leading edge 23, as seen in the direction of rotation of the impeller, which is curved or tapered in order to reduce blood damage. To reduce the likelihood of corrosion and increase the hemo-compatibility, the rotor may be encapsulated or shielded by a polymeric or metal housing. The encapsulation can be provided in a polymeric molding process or by galvanic metal deposition.

Figure 13:
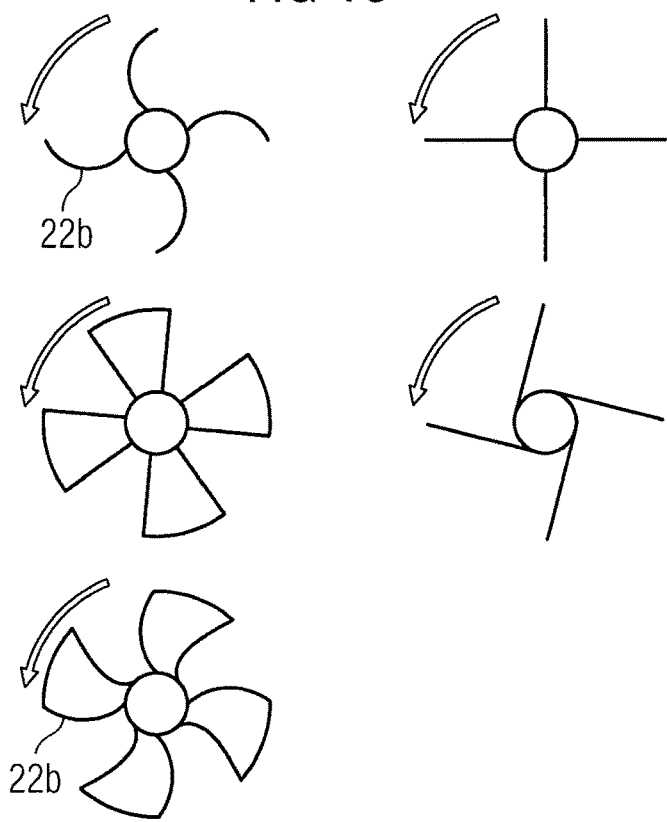

The blade rotor 11 may have more than three blades 15, and the form of the blades 15 need not be triangular or trapezoidal or straight. FIG. 13 schematically shows top views of various blade rotor forms. Among these forms, blade rotors with curved blades are preferred. It is particularly preferred when the leading surface 22b of the impeller blades 15, as seen in the direction of rotation of the impeller, is convex with respect to its radial extension.

Figure 14:
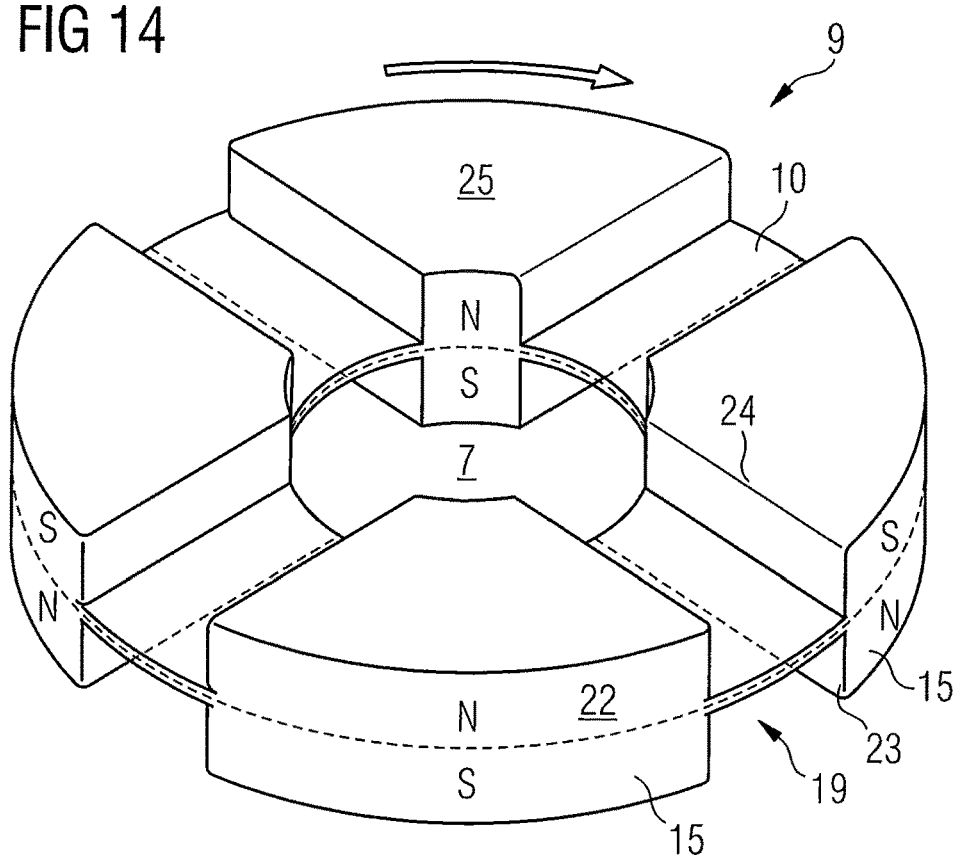
FIG. 14 shows a first variant of an impeller of a second embodiment of the blood pump.

FIG. 14 shows a first variant of an impeller 9 of a second embodiment of a blood pump. The pump casing 1, upper shell 2, lower shell 3, recesses 4, coil assemblies comprising the coils 5 and ceramic plates 6, wall 12 or wall sections within the pump casing 1, through openings 13 extending through the wall 12 or between corresponding wall sections, ring diffuser 20 and blood flow outlet 21 in the second embodiment are identical to those of the first embodiment described above. The only difference in the second embodiment is the impeller 9, which comprises only one disc 10 with a central opening 7, rather than two magnetic discs 10. The disc 10 in the second embodiment is centrally arranged, as seen in an axial direction, and may or may not be magnetic. The blades 15 of the impeller 9 extend axially from both axial sides of the disc 10 and are formed as magnets or may have magnetic regions. Blood flow passages 19 are defined between adjacent blades 15.

In addition, in a variant of the second embodiment, the wall 12 or wall sections arranged within the pump casing may be formed as a radially inward extending wall arranged horizontally, so as to form together with the circular radially outer surface of the central disc 10 the afore-described hydrodynamic radial bearing.

In the first variant of the second embodiment shown in FIG. 14, both the blades 15 and the disc 10 of the impeller 9 are made from magnetized material. The borders between adjacent magnetized regions are indicated by dotted lines. The direction of rotation of the impeller 9 is indicated by an arrow. Here again, the axially extending leading edges of the blades 15 are rounded or tapered so as to enhance the radial hydrodynamic bearing effect and reduce blood damage. In addition, the horizontal leading edges 24 of the blades 15 are also rounded or tapered to enhance the axial hydrodynamic bearing effect and reduce blood damage. Further in addition, although not easy to recognize from the drawing, the upper and lower axial surfaces 25 of the blades are slightly tapered so as to provide a circumferentially extending ramp to create a hydrodynamic axial force lifting the impeller from the respective adjacent wall (not shown) upon rotation of the impeller. Similarly, as has already been explained in connection with the first embodiment, the radially outer surfaces 22 of the blades 15 may likewise change from a smaller radius to a larger radius, as seen in the direction of rotation of the impeller, so as to form, together with the circular wall 12 or circularly arranged wall sections in the pump casing 1, radially converging clearance sections, so as to enhance the radial hydrodynamic bearing effect on the impeller.

Figure 15:
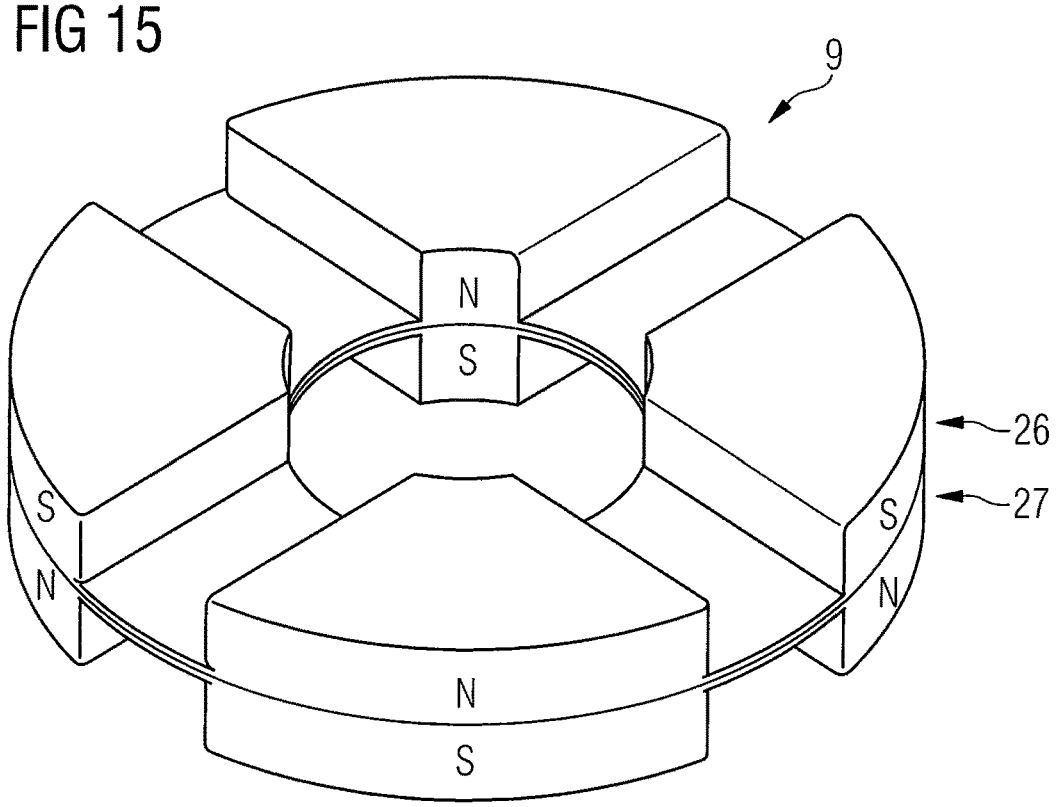
FIG. 15 shows a second variant of the impeller of the second embodiment.

FIG. 15 shows a second variant of the impeller 9 similar to that shown in FIG. 14, except that the disc 10 and the blades 15 are composed of two semi-shells 26, 27 within which the magnets are housed. The semi-shells 26, 27 may be injection molded.

Figure 16:
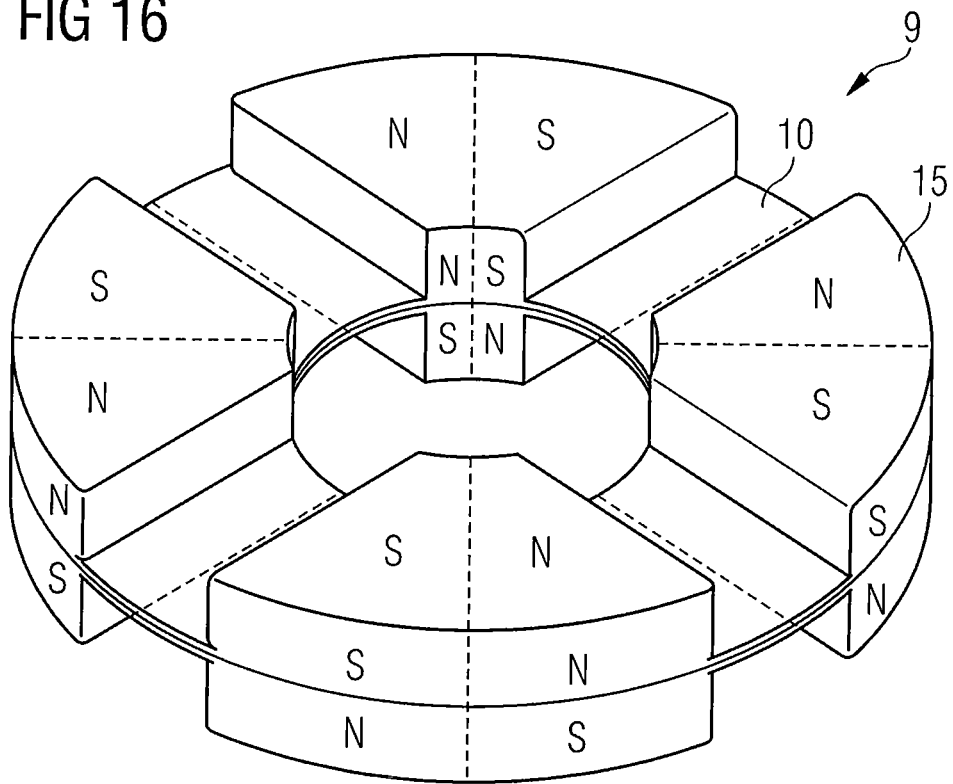
FIG. 16 shows a third variant of the impeller of the second embodiment.

FIG. 16 shows a third variant of the impeller 9 of the second embodiment, similar to the variant shown in FIG. 15. Here, two magnets are housed within each of the blades 15, the alternation of the north and south poles of the respective magnets being indicated with N and S. Again, alternatively both the blades 15 and the disc 10 may be integrally formed from ferromagnetic material and magnetized in sections, as described above in relation to FIG. 14.

Figure 17:
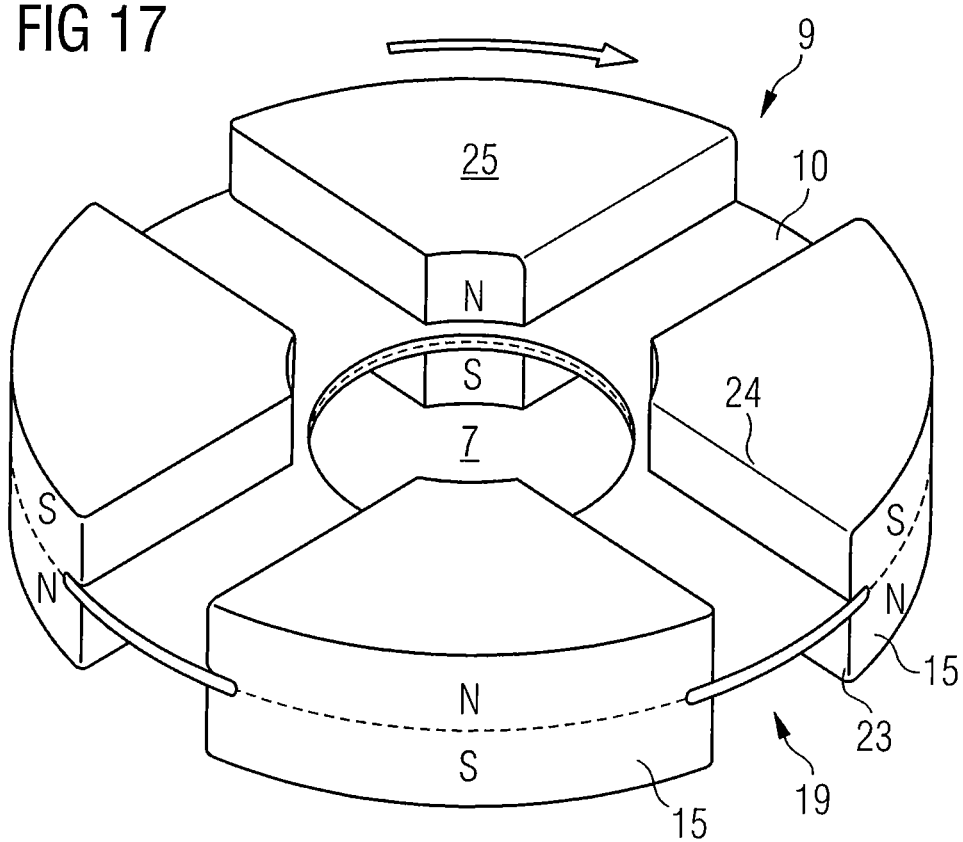
FIG. 17 shows a fourth variant of the impeller of the second embodiment.

Finally, a fourth variant of the impeller 9 of the second embodiment is shown in FIG. 17. This variant is similar to the variant shown in FIG. 14, except that the disc 10 is not necessarily made from a magnetized material. Here the disc 10 may instead be made of a polymer and has a plurality of circularly arranged axial through openings into which the blades 15 are inserted so that they extend from one axial side of the disc 10 to the other axial side thereof.

In all variants of the second embodiment described above, the blades 15 may have a different axial cross section, similar to one of those schematically shown in FIG. 13. However, since only the upper and lower axial surfaces of the blades 15 contribute to the hydrodynamic axial bearing in the second embodiment, blades 15 with a large axial cross section are preferred.

Figure 18:
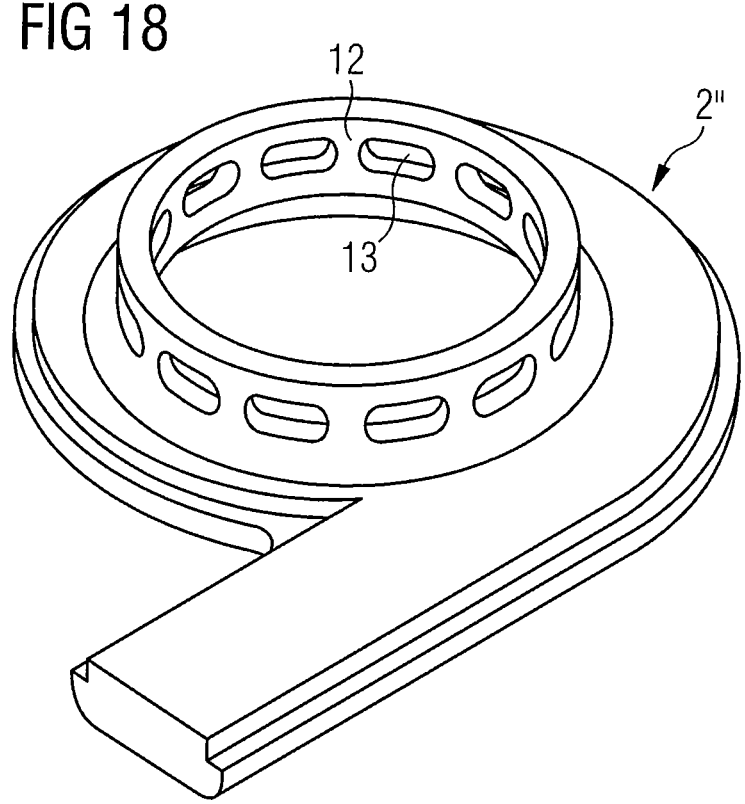
FIG. 18 shows an alternative upper pump housing shell upside down, similar to that of FIG. 5, having a wall with a sufficient thickness such that the openings may serve as a diffuser.
Figure 19:
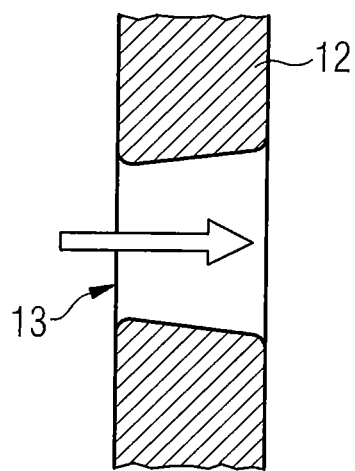
FIG. 19 shows a cross sectional view of the wall of the upper pump housing shown in FIG. 18.

FIG. 18 shows an alternative upper shell 2″ which differs from the upper shell 2′ in FIG. 5 in that the free-standing wall 12 has a greater thickness and the openings 13 are diverging in a radially outward direction. Alternatively (not shown), the free-standing wall 12 may be divided into an upper circular wall section forming part of the upper shell 2 and a lower circular wall section of the lower shell 3, a continuous circular through opening being formed between the two circular wall sections. The continuous circular through opening also may have a diverging or increasing cross-section in a radial outward direction. The increasing cross section is illustrated in FIG. 19 showing a cross sectional view of the wall of FIG. 18 in an axial direction. The blood flows in the direction of the arrow. It is noted that, in case a wall with circumferentially spaced apart openings 13 is provided, the openings preferably also diverge as seen in a radial cross-sectional view. The opening angle is 7° or less in order to avoid detachment of the flow. In this variant the openings 13 or the circular opening serve as a first diffuser providing a pressure increase, i.e. an additional pump effect. The first diffuser may also stabilize the radial hydrodynamic bearing of the impeller by keeping the pressure along the circumference of the impeller constant. For this purpose, the deceleration of the blood in the first diffuser may either be constant or may vary along the circumference of the circular wall 12, for instance by varying the height, width and/or diameter of the openings 13 and/or the wall thickness (i.e., the length of the openings 13).

The invention claimed is:

1. A centrifugal blood pump without a mechanical bearing, comprising:
   a pump casing with a central axis, a blood flow inlet disposed on the central axis and a blood flow outlet disposed on a circumference of the pump casing,
   an impeller arranged in the pump casing so as to be rotatable about the central axis and freely moveable axially and radially within an axial clearance and a radial clearance, the impeller being provided with permanent magnets or permanently magnetized magnetic regions and further with radially extending blades defining passages therebetween for radial blood flow, and
   an electromagnetic drive adapted to cooperate with the permanent magnets or the permanently magnetized magnetic regions of the impeller so as to set the impeller rotating about the central axis,
   wherein the radial clearance is 100 μm or less so as to form a hydrodynamic radial bearing for the impeller, the radial clearance being defined by an outer circumference of the impeller and an inner surface of a plurality of wall sections in a recess of the pump casing, the plurality of wall sections comprising an upper circular wall section and a lower circular wall section, the upper circular wall section and the lower circular wall section being axially spaced apart so as to form a single continuous circumferential through opening for blood to flow from the impeller towards the blood flow outlet, and each of the upper circular wall section and the lower circular wall section comprises pockets, wherein the pockets define regions of differing radial clearance such that the radial clearance is variable between the outer circumference of the impeller and the inner surface of the plurality of wall sections.

2. The centrifugal blood pump according to claim 1, wherein a cross-section of the single continuous circumferential through opening increases in a radially outward direction.

3. The centrifugal blood pump according to claim 1, wherein the electromagnetic drive comprises a plurality of coils without a ferromagnetic core, the plurality of coils being arranged in a plane axially spaced from the impeller.

4. The centrifugal blood pump according to claim 3, wherein the plurality of coils are potted in a polymer matrix.

5. The centrifugal blood pump according to claim 3, wherein the plurality of coils are directly or indirectly mounted on a ceramic plate so as to form an integral component therewith, the ceramic plate limiting the axial clearance.

6. The centrifugal blood pump according to claim 1, wherein the electromagnetic drive comprises a plurality of coils arranged in a plane axially spaced from the impeller on both sides of the impeller.

7. The centrifugal blood pump according to claim 1, wherein the radial clearance is 50 μm or less.

8. The centrifugal blood pump according to claim 1, wherein the impeller comprises a first disc and a second disc which are axially spaced apart from one another, each disc having permanent magnets or permanently magnetized magnetic regions and a central opening arranged for axial blood flow through the first disc and the second disc, the blades of the impeller being arranged between the first disc and the second disc.

9. The centrifugal blood pump according to claim 8, wherein the blades of the impeller are integrally connected by at least one circular rim axially extending from an axial side or both axial sides of the blades and surrounding an outer circumference of at least the first disc and/or the second disc, the circular rim forming a part or all of the outer circumference of the impeller.

10. The centrifugal blood pump according to claim 8, wherein at least the first disc and/or the second disc have a circular outer circumference which forms a part or all of the outer circumference of the impeller.

11. The centrifugal blood pump according to claim 8, wherein each of the first disc and the second disc has a planar disc surface and an adjacent planar wall, wherein the planar disc surfaces of the first disc and the second disc axially face each other and are axially spaced from the respective adjacent planar wall so as to allow blood to flow between the planar disc surfaces and the adjacent planar walls.

12. The centrifugal blood pump according to claim 8, wherein surfaces of the first and second discs which axially face away from each other are each axially spaced from an adjacent wall provided by or arranged in the pump casing so as to allow blood to flow between the surfaces of the first and second discs and the adjacent walls, whereby one or both of the surfaces of the first and second discs and/or one or both of the adjacent walls provide ramps extending about the central axis in a circumferential direction so as to create a hydrodynamic axial force lifting the impeller from the respective adjacent wall upon rotation of the impeller.

13. The centrifugal blood pump according to claim 1, wherein the impeller comprises a disc with a central opening arranged for axial blood flow through the disc and wherein the blades of the impeller extend axially from both axial sides of the disc and are formed as magnets or have magnetic regions.

14. The centrifugal blood pump according to claim 13, wherein the disc has a circular radially outer surface and wherein the plurality of wall sections extend radially inward so as to form together with the circular radially outer surface of the disc the hydrodynamic radial bearing.

15. The centrifugal blood pump according to claim 8, wherein the blades of the impeller have upper and lower surfaces axially spaced from adjacent walls provided by or arranged in the pump casing so as to allow blood to flow between the upper and lower surfaces and the adjacent walls, either or both of the upper and lower surfaces providing a plurality of ramps extending about the central axis in a circumferential direction so as to create a hydrodynamic axial force lifting the impeller from the respective adjacent wall upon rotation of the impeller.

16. The centrifugal blood pump according to claim 15, wherein the plurality of ramps of either or both of the upper and lower surfaces of the blades of the impeller is formed by a curved or tapered leading edge of the blades, as seen in a direction of rotation of the impeller.

17. The centrifugal blood pump according to claim 8, wherein the disc and the blades are composed of two semi-shells within which the permanent magnets or permanently magnetized magnetic regions are housed.

18. The centrifugal blood pump according to claim 8, wherein the first disc, the second disc, and the blades of the impeller are made of magnetized ferromagnetic material.

19. The centrifugal blood pump according to claim 8, wherein the first disc, the second disc and the blades of the impeller are formed as an integral piece of ferromagnetic material, the integral piece of ferromagnetic material being magnetized.

20. The centrifugal blood pump according to claim 1, wherein the blades of the impeller are formed together as an integral injection moulded piece.

21. The centrifugal blood pump according to claim 1, wherein a radial dimension of at least one or all of the blades of the impeller increases circumferentially, radially outer surfaces of these blades forming part or all of the outer circumference of the impeller.

22. The centrifugal blood pump according to claim 1, wherein the blades of the impeller have a leading surface, as seen in a direction of rotation of the impeller, which is convex with respect to its radial extension.

23. The centrifugal blood pump according to claim 1, wherein the blades of the impeller have an axially extending leading edge, as seen in a direction of rotation of the impeller, which is curved or tapered.

24. The centrifugal blood pump according to claim 1, wherein the impeller has an aspect ratio from 4:1 (diameter: height) to 6:1.

25. The centrifugal blood pump according to claim 1, wherein a first magnet or magnetic region and a second magnet or magnetic region, each having a north pole and a south pole, are combined in one impeller blade, with the north and south poles of the first magnet or magnetic region being arranged upside down with respect to the north and south poles of the second magnet or magnetic region.

26. The centrifugal blood pump according to claim 1, wherein the permanent magnets or permanently magnetized magnetic regions have a coating all over that is a polymer or a metal.

27. The centrifugal blood pump according to claim 26, wherein the metal is titanium or a biocompatible precious metal and the coating has a thickness of no more than 50 μm.

28. The centrifugal blood pump according to claim 1, wherein the blood flow outlet is tangentially disposed on a circumference of the pump casing.

29. The centrifugal blood pump according to claim 1, comprising a ring diffuser arranged peripherally of the plurality of wall sections.

30. The centrifugal blood pump according to claim 1, wherein the radial clearance is 20 μm or less.

31. The centrifugal blood pump according to claim 1, wherein the single continuous circumferential through opening is in the form of a ring-like opening increasing in a radially outward direction.

32. The centrifugal blood pump according to claim 31, wherein an opening angle of the ring-like through opening does not exceed 7°.

33. A centrifugal blood pump without a mechanical bearing, comprising:
a pump casing with a central axis, a blood flow inlet disposed on the central axis and a blood flow outlet disposed on a circumference of the pump casing,
an impeller arranged in the pump casing so as to be rotatable about the central axis and freely moveable axially and radially within an axial clearance and a radial clearance, the impeller being provided with permanent magnets or permanently magnetized magnetic regions and further with radially extending blades defining passages therebetween for radial blood flow, and
an electromagnetic drive adapted to cooperate with the permanent magnets or the permanently magnetized magnetic regions of the impeller so as to set the impeller rotating about the central axis,
wherein the radial clearance is 100 μm or less so as to form a hydrodynamic radial bearing for the impeller, the radial clearance being defined by an outer circumference of the impeller and an inner surface of a plurality of wall sections in a recess of the pump casing, the plurality of wall sections comprising an upper circular wall section and a lower circular wall section, the upper circular wall section and the lower circular wall section being axially spaced apart so as to form a single continuous circumferential through opening for blood to flow from the impeller towards the blood flow outlet,
wherein the impeller comprises a first disc and a second disc which are axially spaced apart from one another, each disc having permanent magnets or permanently magnetized magnetic regions and a central opening arranged for axial blood flow through the first disc and the second disc, the blades of the impeller being arranged between the first disc and the second disc, and
wherein the disc has a plurality of circularly arranged axial through openings and wherein the blades are inserted through the circularly arranged through openings so as to extend from one axial side of the disc to the other axial side thereof.

34. The centrifugal blood pump according to claim 33, wherein the disc comprises or is entirely made up of a polymer material.

* * * * *